United States Patent
Borowski et al.

(10) Patent No.: US 6,470,943 B1
(45) Date of Patent: Oct. 29, 2002

(54) APPARATUS FOR MAKING AN ABSORBENT PAD FOR USE IN ABSORBENT ARTICLES

(75) Inventors: Kenneth Thomas Borowski, Appleton; Joseph Michael Kugler, Greenville; James George Van Himbergen, Kimberly, all of WI (US); Norman Earl Brown, Lithonia, GA (US); Leon Eugene Chambers, Jr.; John Christopher Garstka, both of Appleton, WI (US); David Charles Musil, Neenah, WI (US); Edward Erich Werner, Oshkosh, WI (US)

(73) Assignee: Kimberly-Clark Worldwide, Inc., Neenah, WI (US)

( * ) Notice: Subject to any disclaimer, the term of this patent is extended or adjusted under 35 U.S.C. 154(b) by 0 days.

(21) Appl. No.: 09/834,426

(22) Filed: Apr. 13, 2001

Related U.S. Application Data (62) Division of application No. 09/438,134, filed on Nov. 10, 1999, which is a division of application No. 08/874,500, filed on Jun. 13, 1997, now Pat. No. 6,060,115.
(60) Provisional application No. 60/034,426, filed on Dec. 17, 1996.

(51) Int. Cl.[7] .............................................. B32B 35/00
(52) U.S. Cl. ...................... 156/390; 156/501; 156/510; 156/522
(58) Field of Search ............................... 156/167, 242, 156/246, 270, 279, 324, 500, 501, 510, 516, 349, 390, 522; 427/200

(56) References Cited

U.S. PATENT DOCUMENTS

| | | | |
|---|---|---|---|
| 3,721,242 A | 3/1973 | Krusko | 128/287 |
| 3,784,425 A | 1/1974 | Schuster | 156/83 |
| 3,901,238 A | 8/1975 | Gellert et al. | 128/287 |
| 4,035,217 A | * 7/1977 | Kennette et al. | |
| 4,372,312 A | 2/1983 | Fendler et al. | 128/290 R |
| 4,433,024 A | 2/1984 | Eian | 428/198 |
| 4,496,358 A | 1/1985 | Karami et al. | 604/379 |
| 4,573,986 A | 3/1986 | Minetola et al. | 604/366 |
| 4,590,114 A | 5/1986 | Holtman | 428/171 |
| 4,604,313 A | 8/1986 | McFarland et al. | 428/172 |
| 4,785,996 A | 11/1988 | Ziecker et al. | 239/298 |
| 4,806,408 A | 2/1989 | Pierre et al. | 428/76 |
| 4,888,231 A | 12/1989 | Angstadt | 428/213 |

(List continued on next page.)

FOREIGN PATENT DOCUMENTS

| | | |
|---|---|---|
| DE | 41 14 839 A1 | 11/1992 |
| EP | 0 534 863 A1 | 3/1993 |
| EP | 0 658 351 A1 | 6/1995 |
| EP | 0 685 213 A2 | 12/1995 |
| WO | WO 95/31167 | 11/1995 |

*Primary Examiner*—Curtis Mayes
(74) *Attorney, Agent, or Firm*—Wilhelm Law Service; Thomas D. Wilhelm (57) ABSTRACT

Methods and systems for making an absorbent pad for use in an absorbent article utilize a forming device for forming material into an absorbent core, a supply device for supplying a containment layer against the first surface of the absorbent core and spray apparatus for spraying fibers of molten resin onto the second surface of the absorbent core. The fibers form a stabilization layer on the absorbent core that increases the integrity of the absorbent core. The spray apparatus includes a nozzle having a resin aperture for exhausting resin therefrom and multiple gas apertures for exhausting gas therefrom to provide a random pattern to the fibers of molten resin as the fibers are sprayed onto the second surface. Resin can also be sprayed onto first and second portions of the containment layer extending outwardly from edges of the absorbent core so the containment layer and the stabilization layer encompass the absorbent core. In another embodiment, a second containment layer can be placed on the second surface of the absorbent core and first and second stabilization layers can be spaced outwardly therefrom and deposited on the absorbent core.

15 Claims, 9 Drawing Sheets

U.S. PATENT DOCUMENTS

| | | |
|---|---|---|
| 4,904,440 A | 2/1990 | Angstadt .................... 264/517 |
| RE33,481 E | 12/1990 | Ziecker et al. .............. 239/298 |
| 5,069,677 A | 12/1991 | Sakurai et al. .............. 604/370 |
| 5,143,680 A | 9/1992 | Molnar et al. .............. 264/511 |
| 5,194,115 A | 3/1993 | Ramspeck et al. .......... 156/578 |
| 5,227,107 A | 7/1993 | Dickenson et al. ......... 264/113 |
| 5,318,553 A | 6/1994 | Weeks et al. ............... 604/378 |
| 5,387,208 A | 2/1995 | Ashton et al. .............. 604/378 |
| 5,409,768 A | 4/1995 | Dickenson et al. ......... 428/283 |
| 5,417,789 A * | 5/1995 | Lauritzen |
| 5,665,083 A | 9/1997 | Igaue et al. ................. 604/370 |
| H1698 H | 11/1997 | Lloyd et al. ................ 604/378 |
| 5,750,444 A * | 5/1998 | Jarrell et al. |
| 6,060,115 A * | 5/2000 | Borowski et al. |
| 6,069,294 A * | 5/2000 | Leclercq et al. |
| 6,086,950 A * | 7/2000 | Masaki et al. |

\* cited by examiner

APPARATUS FOR MAKING AN ABSORBENT PAD FOR USE IN ABSORBENT ARTICLES

CROSS-REFERENCE TO RELATED APPLICATIONS

This application is a divisional of application, Ser. No. 09/438,134 which was filed on Nov. 10, 1999, which is a divisional application of Ser. No. 08/874,500, filed Jun. 13, 1997, now U.S. Pat. No. 6,060,115, issued May 9, 2000, which claims benefit of provisional application Serial No. 60/034,426, filed on Dec. 17, 1996, all of which are incorporated herein by reference in their entireties.

FIELD OF THE INVENTION

Absorbent articles Such as infant diapers, training pants, adult incontinence products, and the like are well known. Such articles have achieved a wide acceptance due to their ability to receive and absorb body exudates.

BACKGROUND OF THE INVENTION

In general, absorbent articles are formed by multiple webs of material. Such webs generally include a bodyside liner and outer cover on opposing outside surfaces of the absorbent article. An absorbent core generally is located between the bodyside liner and the outer cover. The absorbent core generally has preformed barrier tissue located on a first surface, positioned between the absorbent core and the bodyside liner, and preformed forming tissue located on an opposing second surface, positioned between the absorbent core and the outer cover. The barrier tissue and forming tissue, in combination, completely surround and support the absorbent core.

European Patent Application 0 685 213 A2 published Dec. 6, 1995 discloses depositing fibers onto one surface of absorbent core material to provide a cover. Once the cover of fibers has been deposited and adhered to the absorbent core material, the absorbent core is spirally wound and radially compressed to form a tampon. The fibers at least partially adhere to the surface of the absorbent core material onto which they are deposited. The fibers form an outer cover on the absorbent material.

U.S. Pat. Nos. 5,227,107 and 5,409,768 to Dickenson et al disclose forming devices including forming chambers for forming absorbent structures. The Dickenson et al teachings include meltspraying polymer into the forming chamber, along with other fibers, to form an absorbent core. The meltsprayed polymer is mixed with the absorbent fibers and forms an absorbent structure including meltsprayed fibers dispersed internally in the absorbent core.

SUMMARY OF THE DISCLOSURE

The present invention relates to methods and systems for making absorbent pads for use in absorbent articles. Opposing surfaces of an absorbent core are supported by a pre-formed containment layer and a stabilization layer of resin fiber. More particularly, the methods include forming an absorbent core of material in a forming device, applying the pre-formed containment layer against a first surface of the absorbent core, and depositing the stabilization layer comprising resin fiber onto a second surface of the absorbent core. The resin fiber interacts with the absorbent core at the second surface to increase the integrity of the absorbent core. The first containment layer can be applied to the first surface of the absorbent core prior to depositing the stabilization layer onto the absorbent core or after depositing the stabilization layer onto the absorbent core. The method can be devoid of the step of joining a second previously-formed containment layer with material on the second surface of the absorbent core.

In preferred embodiments, resin fibers are deposited onto the second surface of the absorbent core in a random pattern while the fibers are in such condition that properties of the fibers contribute to securement of the fibers to the absorbent core at the second surface. The resin fibers can comprise polyolefins, such as polypropylene.

In some embodiments, the resin fiber is deposited onto the second surface of the absorbent core using a spray nozzle assembly comprising a plurality of nozzles.

The nozzles in the spray nozzle assembly can be arranged in an array extending across the width of the formed absorbent core. The plurality of nozzles can apply the resin fiber across a width, of the absorbent core, of from about 2.5 inches to about 10 inches. Each nozzle preferably includes a single resin aperture exhausting the resin fiber therefrom, and multiple gas apertures directing the resin fiber exhausted therefrom toward the absorbent core, and imparting a random pattern to each such fiber.

In some embodiments, the resin fibers may be deposited onto the second surface in such condition that some of the fibers bond to the absorbent core at the second surface, and to each other at resin fiber crossing points. The resin fiber directed toward the absorbent core can comprise a spray of molten fibers.

Some embodiments of the method include drawing a vacuum on a rotating forming drum of the forming device and thereby assisting in drawing absorbent material toward the drum in the step of forming the absorbent core.

In most embodiments, the absorbent sausage, including the containment layer and the stabilization layer, is severed at spaced locations along the length thereof, to form individual absorbent pads. The absorbent pad is mounted to a bodyside liner, such that the containment layer is located between the bodyside liner and the absorbent pad. An outer cover is mounted to the second surface of the absorbent pad, such that the stabilization layer is located between the absorbent pad and the outer cover.

In some embodiments, the containment layer has first and second edge portions extending outwardly from the first and second opposing edges of the absorbent core. The fibers of the stabilization layer are deposited onto at least part of the first and second edge portions of the containment layer while the fibers are in condition to contribute to securement of the fibers to the containment layer. The fibers become secured to the containment layer, and subsequent cooling of the fibers causes the fibers to lose their securement characteristic, while retaining securement to the containment layer. The containment layer and stabilization layer can entirely encompass the absorbent core.

Another embodiment includes a system for fabricating an absorbent pad comprising a forming device for forming material into an absorbent core, a supply device for supplying a pre-formed containment layer against the first surface of the absorbent core, and spray apparatus for spraying fibers of molten resin onto the second surface of the absorbent core, thereby depositing a stabilization layer onto the second surface such that the resin fibers interact with the absorbent core to increase the integrity of the absorbent core. The absorbent core can comprise a continuous absorbent sausage, the absorbent sausage being a continuous air formed layer of fiber.

In some embodiments, the forming device includes a fiberizer, a forming chamber and a rotatable forming drum, preferably a vacuum forming drum, for forming the absorbent core. The forming device can also include a scarfing roll for shaving material to reduce the thickness of the absorbent core.

In some embodiments, the spray apparatus includes at least one nozzle having a resin aperture for exhausting resin therefrom, and multiple gas apertures for exhausting gas therefrom. The spray apparatus can comprise a nozzle assembly having a plurality of nozzles depositing molten resin onto the second surface of the absorbent core. The plurality of nozzles can define an array of nozzles extending across the width of the formed absorbent core, and can deposit molten resin across a width, of the absorbent core, of from about 2.5 inches to about 10 inches.

In some embodiments, the spray apparatus comprises a meltspray assembly for directing molten resin toward the second surface of the absorbent core as a spray of molten fibers.

In some embodiments, the system includes a vacuum transfer device for receiving the absorbent core from the forming device prior to application of resin to the second surface of the absorbent core. The first surface of the absorbent core and the corresponding containment layer are disposed toward the vacuum transfer device.

In some embodiments, the system includes a trimming device for trimming the containment layer about the absorbent core.

In some embodiments, an absorbent sausage severing device periodically severs the absorbent sausage, including the containment layer and stabilization layer, to form respective absorbent pads.

In preferred embodiments, a main tacker secures each respective absorbent pad between a respective bodyside liner and a respective outer cover, the stabilization layer being adjacent the outer cover.

In typical embodiments, a severing device periodically severs the bodyside liner and the outer cover to thereby form respective absorbent articles.

In some embodiments, first and second portions of the containment layer extend outwardly from first and second opposing edges of the absorbent core. The spray apparatus deposits resin fiber onto at least part of the first and second portions of the containment layer such that the resin fiber interacts with the containment layer, thereby contributing to securement of the resin fiber to the containment layer.

In another embodiment, the system makes an absorbent article comprising a chassis. The chassis is formed of an outer cover, and a bodyside liner mounted to the outer cover and contacting the body of a user. An absorbent core is disposed between the bodyside liner and the outer cover. A pre-formed containment layer is disposed between the bodyside liner and the first surface of the absorbent core. A stabilization layer of resin fiber is disposed between the absorbent core and the outer cover. The stabilization layer interacts with the absorbent core at the second surface to increase the integrity of the absorbent core.

In most embodiments, the stabilization layer comprises fibers deposited on the second surface in a random pattern, properties of the fibers contributing to securement to the second surface. The fibers are typically secured to each other at crossover points. The fibers can comprise polymeric material.

In some embodiments, the containment layer has first and second portions extending outwardly from opposing edges of the absorbent core, the stabilization layer being secured to the containment layer at at least part of the first and second portions, the containment layer and the stabilization layer, in combination, encompassing the absorbent core.

In most embodiments, the containment layer comprises barrier tissue and the stabilization layer comprises a material that is not generally considered to be an adhesive.

In another embodiment a narrow second containment layer is placed along the length of the second surface of the absorbent core. First and second stabilization layers are then spaced on either side of the second containment layer. The stabilization layers can be secured to only the absorbent core, or more nozzles can be selected such that the molten fibers of the first and second stabilization layers can contact the second containment layer and the first containment layer thus securing the containment layers to the absorbent core.

The invention is not limited in its application to the details of the construction and the arrangement of the components set forth in the following description or illustrated in the drawings. The invention is capable of other embodiments or of being practiced or carried out in various ways. Also, it is to be understood that the terminology and phraseology employed herein is for purpose of description and illustration and should not be regarded as limiting. Like reference numerals are used to indicate like components. The drawings are for purposes of illustration, and are not necessarily drawn to scale.

DETAILED DESCRIPTION OF THE ILLUSTRATED EMBODIMENTS

The present invention is directed toward methods and systems for making an absorbent pad for use in an absorbent article. An exemplary method replaces forming tissue with sprayed molten resin to increase the integrity of the absorbent core. Such practice maintains the overall integrity of the absorbent article while reducing the cost of production.

Figure 1:
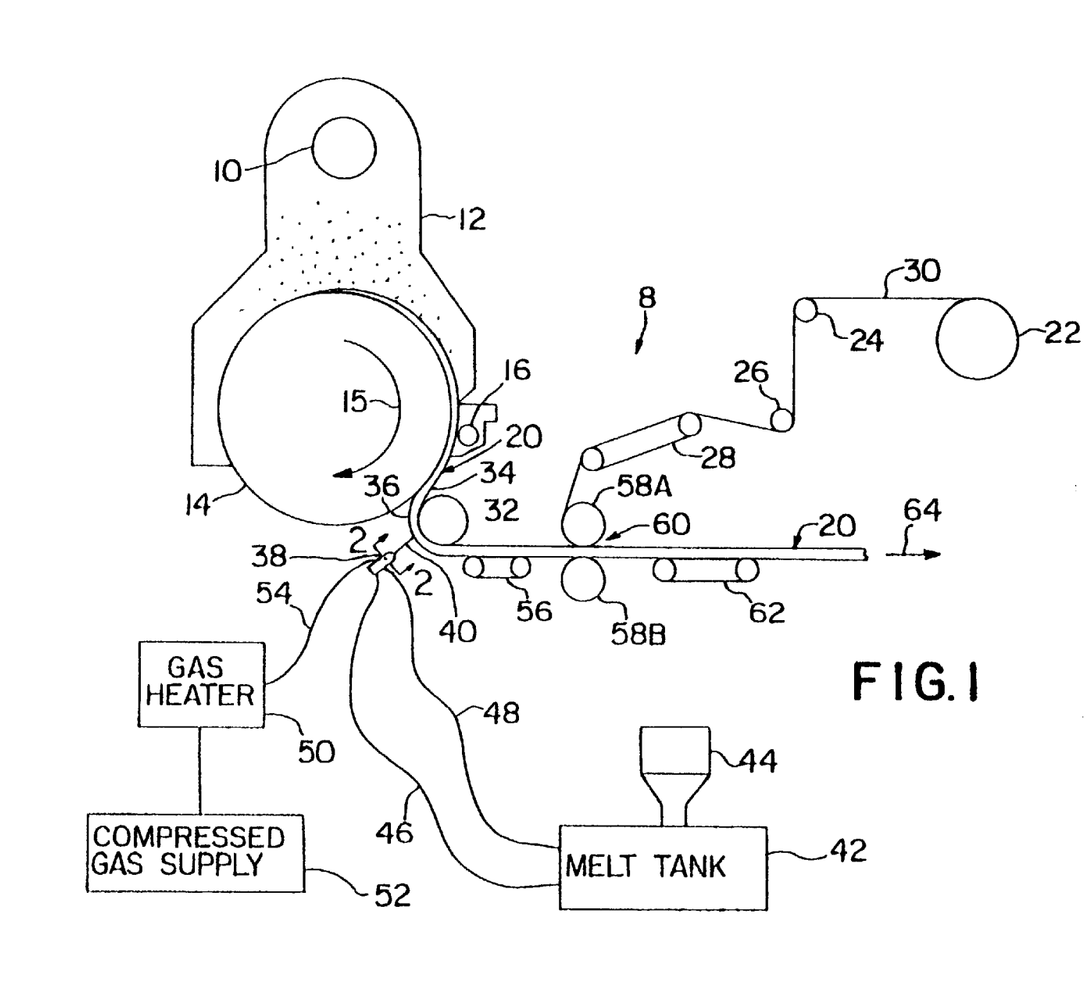
FIG. 1 shows diagrammatically a system for making an absorbent pad of the invention for use in an absorbent article.

FIG. 1 shows a first system 8 for fabricating an absorbent core. System 8 includes a fiberizer 10, contained in a forming chamber 12 for receiving absorbent material, and a forming drum 14 which rotates, generally continuously, in the direction of arrow 15. System 8 also includes a scarfing roll 16. Scarfing roll 16 shaves excess absorbent material from an absorbent sausage 20 formed by forming drum 14. A vacuum transfer device 32 delivers absorbent sausage to nip rolls 58A, 58B. A supply device 22, turning rolls 24, 26, and transfer conveyor 28, deliver a pre-formed containment layer 30 to nip roll 58A. At nip rolls 58A, 58B, containment layer 30 is secured to a first surface 34 of absorbent sausage 20.

A heated melt tank 42 receives particulate resin from a storage hopper 44 and heats the resin to a molten state. A heated resin delivery line 46 delivers the melted thermoplastic resin to a heated spray nozzle assembly 38. A heated recirculation line 48 recirculates unused resin back to melt tank 42 for reuse.

A compressed gas supply 52 supplies compressed gas to a gas heater 50. Gas heater 50 heats the compressed gas, as necessary. A supply line 54 supplies the heated compressed gas to spray nozzle assembly 38. A spray nozzle assembly 38 sprays a resin fiber 40 onto a second surface 36 of absorbent sausage 20 to form a stabilization layer 65.

In the context of the invention, "absorbent sausage" refers to any absorbent material or combination of absorbent materials having a generally continuous length, and can also include superabsorbent materials.

"Absorbent pads" refers to cut lengths of the absorbent sausage, including containment layer 30 and stabilization layer 65, that can be placed in absorbent articles.

Figure 14:
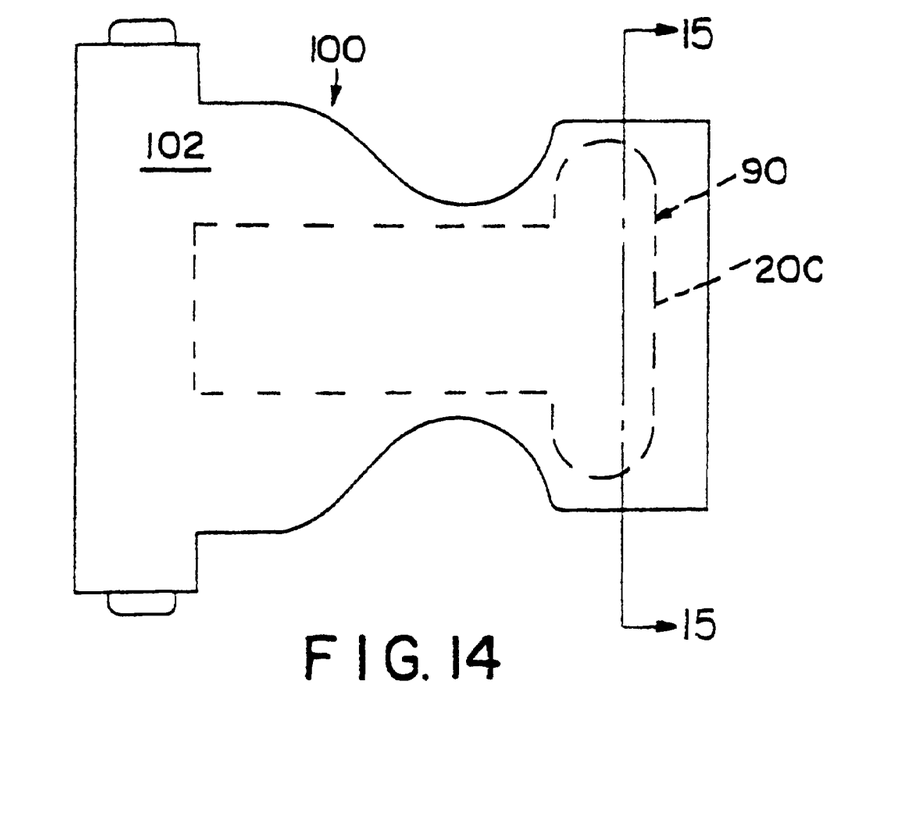
FIG. 14 shows a top view of a completed absorbent article made with an absorbent pad of the invention.

"Absorbent core" 20C, shown in FIG. 14, refers to an appointed fibrous batt segment individually formed on forming drum 14. Absorbent core 20C includes absorbent material used for forming the absorbent sausage, but does not include any stabilization layer or containment layer applied thereto.

Absorbent sausage 20 is deposited from vacuum transfer device 32 onto transfer conveyor 56, and advances on the transfer conveyor toward first and second nip rolls 58A, 58B comprising debulker 60. At debulker 60 the preformed containment layer is secured to absorbent sausage 20. Absorbent sausage 20 then advances to transfer conveyor 62. Arrow 64 indicates a path leading absorbent sausage 20 toward further processing stations not shown in FIG. 1.

Fiberizer 10 fiberizes absorbent material in forming chamber 12. Thus fiberizer 10 breaks up boards of fiber material to form individualized fluff. Absorbent sausage 20 comprises a matrix of generally hydrophilic fibers, such as a web of cellulosic fluff, preferably in combination with a particulate highabsorbency material commonly known as superabsorbent material. In a particular embodiment, absorbent sausage 20 comprises a mixture of superabsorbent hydrogel-forming particles and wood pulp fluff fibers. In place of the wood pulp fluff, one may use any of a variety of synthetic fibers, a combination of synthetic fibers, or a combination of synthetic fibers and natural fibers. At least part of the absorbency of the absorbent material can also be derived from capillary action resulting from the arrangement of fibers with respect to each other. Absorbent sausage 20 preferably does not contain any meltsprayed polymeric material internal to its structure. Absorbent sausage 20 preferably comprises a continuous layer of air formed fiber.

Forming drum 14 forms absorbent sausage 20 using gravity, and a vacuum chamber (not shown) contained in the forming drum. A vacuum generating apparatus (not shown) generates an air flow which, in combination with the vacuum chamber and apertures (not shown) in the forming surface of forming drum 14, assists in drawing absorbent material 18 onto the forming surface of the drum. The amount of vacuum supplied by the vacuum generating apparatus can be varied, turned off, or blocked, to meet the specific needs of the particular absorbent sausage 20 being formed. For instance, at the point absorbent sausage 20 must be released and transferred to vacuum transfer device 32, the vacuum at the area of transfer can be blocked on forming drum 14. One example of forming devices for use with the invention is set forth in FIGS. 17–19 of U.S. Pat. No. 5,227,107, the disclosure of which is hereby incorporated by reference in its entirety.

In most embodiments, forming drum 14 comprises a first sausage carrier, and vacuum transfer device 32 comprises a second sausage carrier. In certain instances, formed absorbent sausage 20 may desirably be contoured in shape, or shaved to reduce thickness. As suggested by FIG. 1, scarfing roll 16 shaves absorbent sausage 20 while the sausage is on forming drum 14, and before transfer of the absorbent sausage to vacuum transfer device 32.

Figure 2:
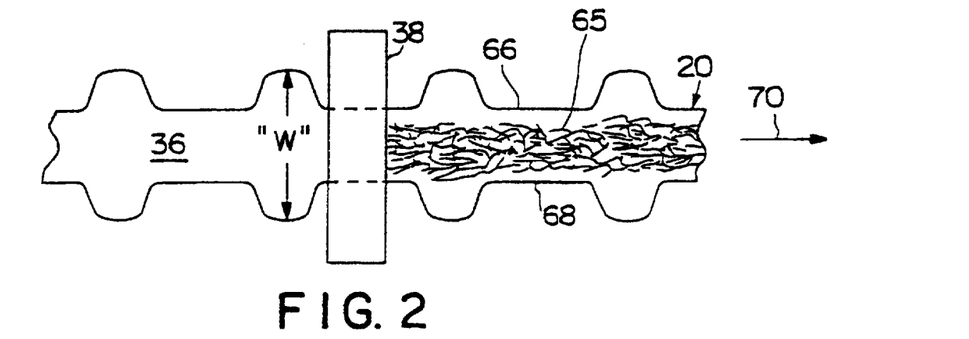
FIG. 2 shows a top view of a length of an absorbent sausage, and a spray nozzle assembly, taken at 2—2 of FIG. 1.
Figure 3:
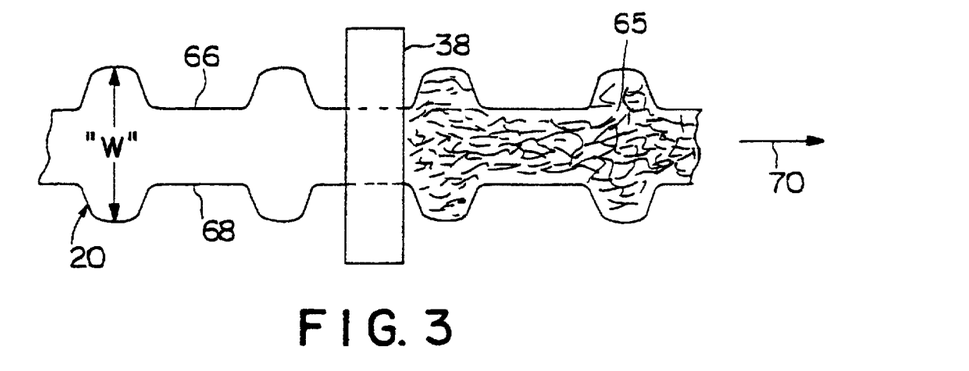
FIG. 3 shows a top view as in FIG. 2 wherein the resin is applied over a greater width of the combination of the absorbent sausage.

While FIGS. 1–3 show absorbent sausage 20 as a continuous web of material, absorbent cores of absorbent material 18 can also be formed as separate individual cores on forming drum 14. Such an arrangement obviates severing at spaced locations of absorbent sausage 20 to create individual absorbent cores at a later step. In any event air laid absorbent cores are formed directly on forming drum 14.

The vacuum apertures (not shown) on forming drum 14 can be arranged such that forming chamber 12 forms a shaped absorbent sausage 20. Absorbent sausage 20 can, for example, be formed in a "r" shape, as shown in FIGS. 2, 3, 8, 9, 11, 11A, 13, and 14, an hourglass shape, or any other shape useful for an absorbent article.

Pre-formed containment layer 30 preferably comprises barrier tissue. A typical such barrier tissue is a single-ply, low porosity creped wadding or the like. Other tissues can also function as the containment layer provided the proper porosity and other characteristics are present An exemplary barrier tissue has a basis weight of 12.5 pounds/ream, a porosity of approximately 90 cubic feet per minute per foot squared, and strength of about 500 grams.

Containment layer 30 is drawn around turning rolls 24, 26 and on transfer conveyor 28 to nip roll 58A. Nip rolls 58A, 58B place containment layer on first surface 34 of absorbent sausage. 20.

In another potential embodiment (not shown), containment layer 30 advances from conveyor 28 to an outer surface of vacuum transfer device 32. After placement of containment layer 30 on vacuum transfer device 32, or almost simultaneously therewith, absorbent sausage 20 is transferred onto vacuum transfer device 32. A second vacuum generating apparatus (not shown) assists vacuum transfer device 32 in maintaining containment layer 30 and absorbent sausage 20 thereon. The porosity of containment layer 30 must be sufficient to allow enough vacuum through the containment layer to support absorbent sausage 20 on vacuum transfer device 32. This is so because the containment layer generally is positioned between the first surface 34 of the absorbent sausage and the outer surface of vacuum transfer device 32. Thus such an embodiment is not contemplated as being particularly effective unless the porosity of containment layer 30 is very large.

While vacuum transfer device 32 supports absorbent sausage 20, spray nozzle assembly 38 deposits molten and/or semi-molten resin fibers 40 onto opposing second surface 36 of absorbent sausage 20, thereby forming stabilization layer 65. FIG. 2 shows spray nozzle assembly 38 applying resin fiber 40 along a continuous length of a middle section of absorbent sausage-20 between opposing outside edges 66, 68 of the absorbent sausage. Arrow 70 represents the direction of movement of absorbent sausage 20 in the process. Resin fiber 40 quickly cools and hardens to form stabilization layer 65.

In the embodiment of FIG. 2, for example, the system of FIG. 1 deposits resin fibers 40 at the central portion of absorbent sausage 20 to form stabilization layer 65. In this embodiment not all of the individual nozzles of spray nozzle assembly 38 need operate to deposit resin fiber 40.

In the embodiment of FIG. 3, more individual nozzles of spray nozzle assembly 38 deposit resin fibers 40 across the entire width "W" of absorbent sausage 20. Thus, some amount of meltspray between ears 21 of absorbent sausage 20 is overspray and wasted. In later embodiments, when the meltspray is applied, containment layer 30 is in surface-to-surface contact with the opposite surface of absorbent sausage 20 and thus receives the overspray. In such an arrangement, the overspray secures stabilization layer 65 to containment layer 30.

In other embodiments, spray nozzle assembly 38 includes at least some intermittently operated individual nozzles that form the spray pattern that corresponds to the shape of the absorbent sausage 20 with minimal overspray. Thus, the amount of resin fibers 40 utilized can be conserved and the cost of the process reduced.

Figure 4:
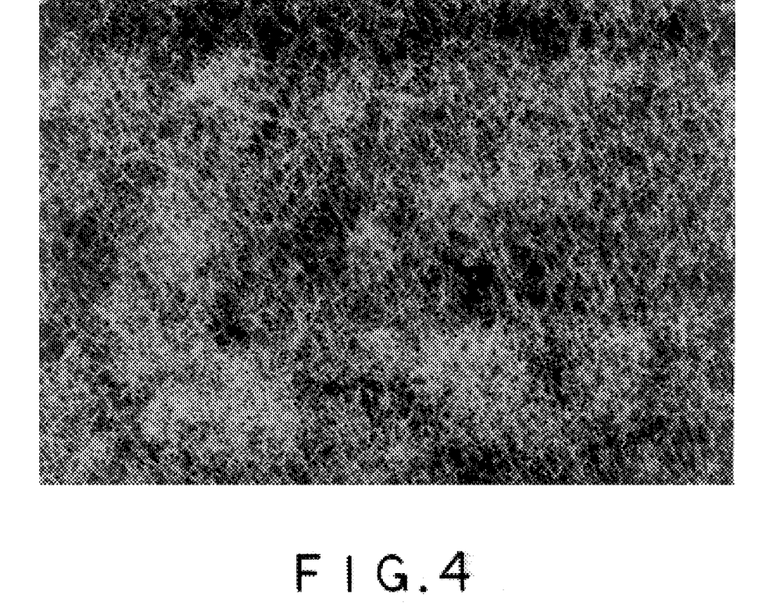
FIG. 4 shows a photomicrograph of a section of an actual representative stabilization layer of FIG. 3.

Stabilization layer 65 shown deposited on second surface 36 of absorbent sausage 20 in FIGS. 2 and 3 is for purposes of illustration only. FIG. 4 shows a detailed photomicrograph showing a section of an actual representative stabilization layer 65. Stabilization layer 65 preferably comprises resin fibers 40 which are composed of multiple individual fibers forming a random web-like pattern as shown in FIG. 4. At crossing points where one fiber intersects another, the molten fibers directly bond to one another without adhesive. Stabilization layer 65 is permeable to liquids and gases. Where the molten resin fibers 40 contact second surface 36 of absorbent sausage 20, the fibers can interact with the individual absorbent fluff fibers to increase the integrity of the absorbent sausage structure. For instance, molten resin fibers 40 may have sufficient tackiness and deformability to conform to and mechanically bond to the fibers in absorbent sausage 20, or containment layer 30, if it is present when meltspraying occurs. Desirably, fibers 40 have substantially no adhesive or tacky characteristics after cooling to ambient temperature. The direct bonding of fibers 40 to second surface 36 of absorbent sausage 20 preferably occurs before the fibers are fully cooled. Fibers 40 cool very quickly toward room temperature, which solidifies and hardens the fibers. Fibers 40 first cool on their outer surface while the interior of the fibers remains molten for a longer period of time. As a result, fibers 40 tend to deform and wrap about the fluff fibers of the absorbent material. Therefore, thicker fibers 40 tend to perform better than thinner fibers with respect to deformation and securement to absorbent sausage 20. The ability to deform, and other properties of fibers 40, assist in stabilizing the fluff fibers and as a result help contain fluff fibers and superabsorbent material within absorbent sausage 20. Thus fibers 40 form stabilization layer 65 and are secured to absorbent sausage 20 at second surface 36.

The random weblike pattern of stabilization layer 65 shown in FIG. 4, and the structural characteristics of fibers 40 which make up the layer assist in stabilization of the absorbent material, including fluff fibers and any superabsorbent material, of absorbent sausage 20. Therefore, the random weblike pattern of stabilization layer 65 improves the overall integrity of absorbent sausage 20. Stabilization layer 65 also helps to protect the outer cover from e.g. penetration by particles of superabsorbent material. Therefore, stabilization layer 65 of fibers 40 replaces the use of forming tissue between an absorbent core and an outer cover in an absorbent article. Thus the system and method are typically devoid of joining a previously-formed containment layer with the absorbent material on second surface 36 of absorbent sausage 20. Further, depositing resin fibers 40 as stabilization layer 65 is less expensive than applying a preformed tissue layer to absorbent sausage 20. In a preferred embodiment, stabilization layer 65, on absorbent sausage 20, has a weight of about 2 to about 12 grams per square meter.

In the context of the invention, the term "resin" refers to any solid or liquid organic material of natural or synthetic origin that has a melting point and is generally polymeric. The thermoplastic resin can comprise polymers such as polyolefins. For instance, the resin can comprise polyethylene, polypropylene, or the like. Further, the thermoplastic resin can comprise combinations of various polymers. The melting point or points of resin fibers 40 typically are in a range between about 140 degrees Celsius and about 260 degrees Celsius.

European Patent Application 0 658 351A1 to Korpman, published Jun. 21, 1995, is hereby incorporated by reference in its entirety. Korpman discloses thermoplastic polymers that can be utilized in forming microfibers effective in some embodiments of the invention. Desirably the thermoplastic resins used to form stabilization layer 65 of the invention do not include pressure sensitive adhesive materials in amounts which could, by themselves activate securement or other attachment of stabilization layer 65 to absorbent core 20 or a bodyside liner. Neither do they include a similar amount of any other composition generally known as an adhesive material.

The overall spray apparatus for applying fibers 40 is preferably a meltspray apparatus. Exemplary such meltspray apparatus includes melt tank 42 which receives particulate resin material from hopper 44. A preferred melt tank comprises a grid melter, Model MX40110, manufactured by Nordson Corp. of Duluth, Ga.

Melt tank 42 includes a heating apparatus (not shown) for melting the thermoplastic resin and maintaining the resin in a molten state. Melt tank 42 maintains thermoplastic resin at a desired temperature. Heated resin delivery line 46 delivers molten resin to spray nozzle assembly 38. Heated resin recirculation line 48 returns excess molten resin to melt tank 42. Ongoing circulation of resin through lines 46 and 48 helps maintain appropriate temperature and pressure in spray nozzle assembly 38, and thus prevents cooling and hardening of the resin inside the spray nozzle assembly or delivery line 46. For example, if spray nozzle assembly 38 stops spraying thermoplastic resin fibers 40, recirculation line 48 and delivery line 46, in combination, continuously provide molten resin to the spray nozzle assembly. Further, the temperature of thermoplastic resin in spray nozzle assembly 38 can be readily controlled, and dynamically adjusted, by adjusting the rate of flow of resin through lines 46, 48 and/or by adjusting the temperature of the resin in melt tank 42. The temperature of polypropylene resin preferably is between about 204 degrees Celsius and about 232 degrees Celsius.

Compressed gas supply 52 provides compressed gas to gas heater 50. Gas heater 50 heats the compressed gas to the desired temperature. Heated gas supply line 54 carries the heated compressed gas from gas heater 50 to spray nozzle assembly 38. The compressed gas is delivered to nozzle assembly 38 to control the pattern of fibers 40 being applied to absorbent sausage 20 as will be described later in greater detail. The compressed gas preferably is heated to a temperature similar to the temperature of the resins being applied to the absorbent sausage 20 and at a pressure of about 40 to about 70 pounds per square inch gauge (PSIG).

Figure 5:
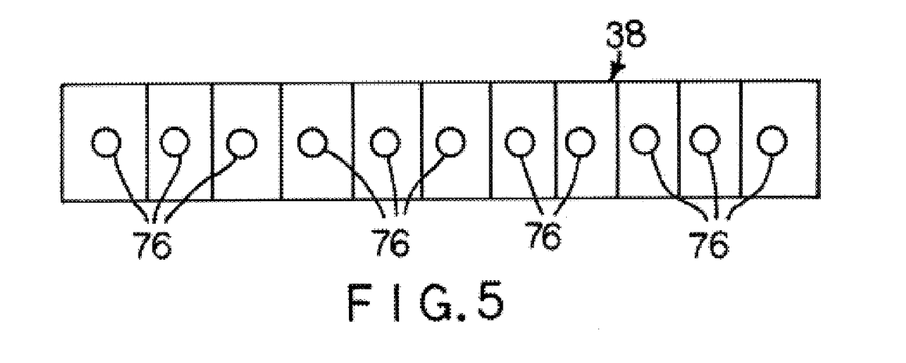
FIG. 5 shows representatively, the arrangement of the nozzles in the spray nozzle assembly, as viewed from the vacuum transfer device.

FIG. 5 shows the side of spray nozzle assembly 38 which faces absorbent sausage 20. An array of eleven nozzles 76 is shown extending across the length of spray nozzle assembly 38. Each nozzle 76 can be considered a separate module and is supplied with molten resin via a gear pump. As shown in FIGS. 2 and 3, spray nozzle assembly 38 is positioned so nozzles 76 are located at spaced locations across the width "W" of absorbent sausage 20 and containment layer 30. As a result, selected nozzles 76 can exhaust resin fibers 40 across the width "W" of absorbent sausage 20 to form stabilization layer 65.

While eleven nozzles are shown, any number of nozzles can be utilized. Similarly, one or more of the nozzles in a nozzle array may be blocked off to limit the number of nozzles used for a particular operation. For example, fewer nozzles (such as three nozzles) may be used to form the narrow spray pattern of stabilization layer 65 shown in FIG. 2, and more nozzles (such as five nozzles) may be used to form the wider spray pattern indicated for stabilization layer 65 shown in FIG. 3. Further, while FIG. 5 shows one row of nozzles 76, second and additional rows can be utilized to increase the amount of material used to form stabilization layer 65 on second surface 36 of absorbent sausage 20, or the rate at which material is applied, or to provide more uniform distribution of such material. For instance, in one preferred arrangement, a second row of eleven nozzles (not shown) aligned in the machine direction and offset in the cross machine direction from the first row of nozzles 76 can be provided in addition to the first row of nozzles. In a typical meltspray embodiment, the individual nozzles comprise modules spaced approximately one inch apart.

The number and spacing of nozzles 76 in spray nozzle assembly 38 is sufficient to permit the application of stabilization layer 65 across a width of the absorbent sausage 20 preferably from about 2.5 inches (narrow spray pattern) to at least about 10 inches (wide spray pattern). Additional nozzle assemblies can be used to apply a wider stabilization layer 66 across a wider width of an absorbent core, a containment layer 30, or other base web. Further, nozzles 76 need not be arranged in a linear array. Thus, nozzles 76 can be arranged in a virtually unlimited number of nozzle patterns so long as the nozzles provide sufficient quantity of fibers 40 distributed on the underlying substrate in a desired weight and a desired pattern, typically a uniform distribution pattern. Individual nozzles 76 can be controlled, e.g., intermittent operation, to vary the width and area covered by the spray patterns. Further, the amount of resin being deposited by individual nozzles 76 can also be controlled.

Nozzles 76 can be controlled such that heavier application of fibers 40 occurs in some areas of absorbent sausage 20, and less heavy application of fibers 40 occurs in other areas on second surface 36 of absorbent sausage 20. For example, in the embodiment of FIG. 3, increased fibers 40 can be applied in the middle of absorbent sausage 20 and a smaller quantity of fibers 40 can be applied at the ears of the absorbent sausage. Thus the amount of fibers 40 can be varied in the cross-direction of absorbent sausage 20. This arrangement conserves the amount of molten fibers 40 applied to form stabilization layer 65 and reduces the overall cost of products so formed.

In other embodiments, nozzles 76 can be intermittently operated to vary the amount of fibers 40 applied in the machine direction. For example, in the embodiment of FIG. 14, fibers 40 can be randomly applied to absorbent pad 90 at locations where the pad is present and not applied at locations where the pad is not present during formation of the absorbent article. This arrangement conserves the amount of fiber 40 applied to form stabilization layer 65 and thus reduces the cost of products made by this process.

Figure 6:
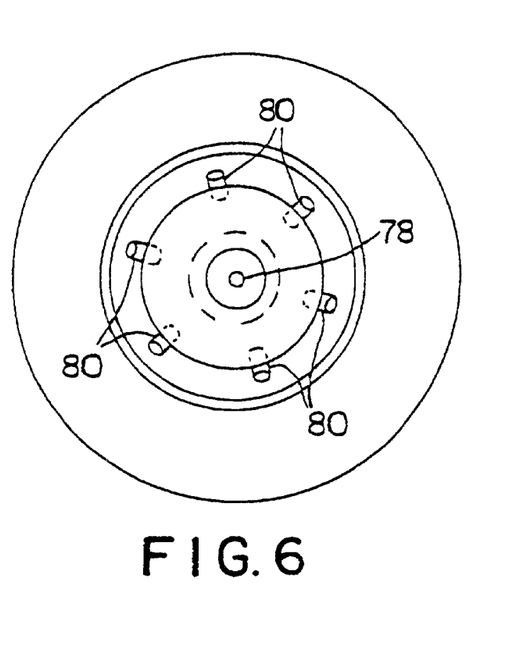
FIG. 6 shows the resin fiber output end of a single nozzle useful in the invention.

FIG. 6 shows the output end of a single exemplary nozzle 76 of spray nozzle assembly 38. Nozzle 76 includes a single resin aperture 78 for exhausting resin fiber 40. Multiple gas apertures 80 are generally -evenly spaced about resin aperture 78. Resin aperture 78 preferably is centered on the output end of nozzle 76. In a preferred nozzle, resin aperture 78 has a diameter of about 0.025 inch and gas apertures 80 have diameters of about 0.030 inch. In operation, gas apertures 80 continuously exhaust gas which control the application of resin fiber 40 to absorbent sausage 20. The design of the nozzle 76, i.e., the diameter of resin aperture 78, and the diameter and angle of gas apertures 80 cause random movement of fiber 40. The random movement of resin fiber 40 creates the random weblike pattern exemplified in stabilization layer 65 and shown in FIG. 4. Compressed gas aperture 80 preferably has a total throughput of between about 0.4 and about 0.8 standard cubic feet per minute. Resin aperture 78 preferably has a total throughput of between about 3 pounds per inch per hour and about 5 pounds per inch per hour of resin fiber 40 for the meltspray embodiment While the preferred gas is air, other gases and mixtures of gases can be utilized. The compressed gas attenuates the resin exiting resin aperture 78, thus to form elongated, and correspondingly thinned, resin fibers 40. To the extent gas apertures 80 are of a different diameter than the above recited 0.030 inch, the velocity and flow of gas exhausted from the respective apertures is changed, causing the fibers to be drawn more or less severely. Such drawing changes the diameter of the resultant fibers 40.

Multiple gas apertures 80 and resin aperture 78, in combination, spray molten resin fibers having a random pattern. Such fibers are soft when sprayed. In forming stabilization layer 65, illustrated, multiple nozzles 76 exhaust a corresponding multiple number of fibers. Gas from multiple gas apertures 80 imparts random patterns to the multiple fibers which, in combination, form the weblike pattern of stabilization layer 65 shown in FIG. 4. While six gas apertures are shown for a given nozzle in FIG. 6, more or fewer gas apertures can be utilized, so long as the exhaust gas from the gas apertures of a given nozzle effectively controls resin fiber 40 being exhausted from resin aperture 78. The resin fibers so formed typically have a diameter from about 8 microns to about 73 microns, and preferably fiber diameters sized from about 20 microns to about 40 microns. Fibers larger than 80 microns tend to be tactually noticeable to the user of the absorbent article made therefrom. Thus, larger fibers tend to impact negatively on the overall comfort and aesthetics of an absorbent article so constructed. The resin fibers generally are continuous in length when meltsprayed onto a substrate, such as second surface 36 of absorbent sausage 20 or containment layer 30.

Meltspray systems can include a separate gear pump stream (not shown) for each nozzle 76 or module to deliver resin fibers 40 under pressure toward absorbent sausage 20.

Heated resin delivery line 46, heated resin recirculation line 48 and gas heater 50 allow the meltspray system to maintain temperature of thermoplastic resin, even when meltspray is applied intermittently or shutdown for an extended period of time. Thus, upon restart, the meltspray system generates very little waste material as compared to a corresponding meltblowing system. One example of intermittent or pulsed operation of meltspray nozzle assembly 38 can be for providing no resin, or less resin, on an area of absorbent sausage 20 that is away from the crotch portion of the final absorbent article, and therefore requires less integrity.

Other equipment which can be utilized for spray nozzle assembly 38 can be found in columns 14–16 of U.S. Pat. No. 5,227,107. European Patent Application 0 685 213A2 published Dec. 6, 1995, and hereby incorporated by reference in its entirety, discloses specific meltspray equipment and some resin materials useful in the invention.

Another exemplary adhesive spray assembly and nozzle is set forth in U.S. Pat. No. 4,785,996 to Ziecker et al, the disclosure of which is hereby incorporated by reference in its entirety. FIGS. 2 and 3 especially, show details of an exemplary nozzle useful for applicants' invention.

Meltblowing apparatus, while less preferred, can also be utilized with the invention. Typical meltblowing devices have orifices on the order of about 0.0145 inch in diameter, and have 30 or so such orifices per cross-directional inch of a die tip, and two opposing air slots configured on each side. Like meltspray, once high pressure air exits the die tip, it rapidly expands, thus attenuating the molten resin streams exiting the respective die tip. For applicants' invention, the meltblowing apparatus must output fibers having a diameter of at least 8 microns. Smaller diameter fibers tend to form an impermeable layer on absorbent sausage 20. Smaller fibers also tend to deform less, and thus, conform less to the surface of the absorbent sausage.

Meltblowing apparatuses useful in the present invention receive heated resins from a melt tank and apply the resins to a material, but have no recirculation means. Therefore, meltspray apparatuses generally have a quicker start-up time and reach operating pressure sooner than meltblowing systems.

Melt tank 42, gas heater 50, and spray nozzle assembly 38 generally are controlled by a conventional central controller (not shown), such as an ANAPHASE® controller made by Nordson Corp. of Duluth, Ga. Such electrical controllers include panel annunciator alarms, status indicators, control switches, and other control mechanisms. The central controller can monitor and control all temperatures including the temperatures in melt tank 42, resin delivery line 46, resin recirculation line 48 and gas heater 50.

Debulker 60 generally comprises a nip formed by rolls 58A, 58B. Debulker 60 controls the thickness of absorbent sausage 20 by compressing the sausage in the nip, between rolls 58A, 58B. Debulkers are well known conventional devices that can be utilized for controlling the thickness of absorbent pads.

After containment layer 30 is applied to first surface 34, and stabilization layer 65 is deposited onto second surface 36, absorbent sausage 20 passes through debulker 60, and the absorbent sausage advances along path 64 for further processing.

Figure 7:
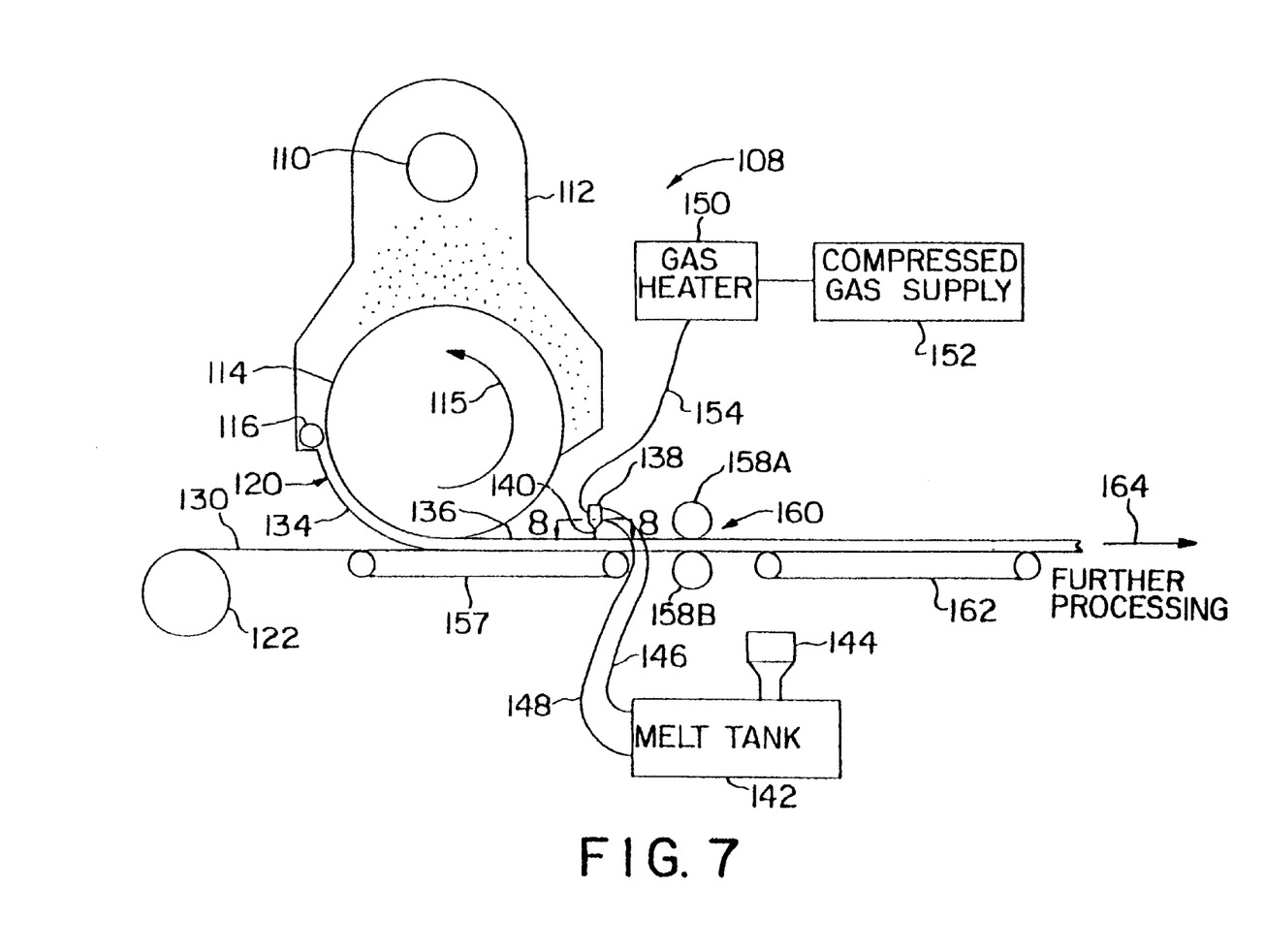
FIG. 7 shows a second embodiment of systems of the invention for making an absorbent pad.

FIG. 7 shows a second embodiment of the invention wherein the prefix "1" on the element numbers indicates the second embodiment. Second and third digits are used in common with the first embodiment to represent structure corresponding to like structures in the first embodiment. System 108 includes fiberizer 110 which breaks up fiber board into absorbent material and ejects it into forming chamber 112 and deposits it on forming drum 114. Forming drum 114 generally continuously rotates in the direction of arrow 115. Forming drum 114 has a scarfing roll 116 nearby which shaves absorbent material to reduce the thickness of absorbent sausage 120. Supply device 122 supplies containment layer 130 to transfer conveyor 157. In this embodiment, transfer conveyor 157 receives containment layer 130 and receives absorbent sausage 120 adjacent the containment layer. First surface 134 of absorbent sausage 120 contacts containment layer 130. Second surface 136 of absorbent sausage 120 adjacent the spray nozzle assembly 138 receives resin fiber 140. Heated melt tank 142 receives particulate resin from a storage hopper 144 and heats it to a molten state. A heated resin delivery line 146 delivers melted thermoplastic resin to spray nozzle assembly 138. A heated recirculation line 148 recirculates unused resin back to melt tank 142 for reuse.

Figure 12:
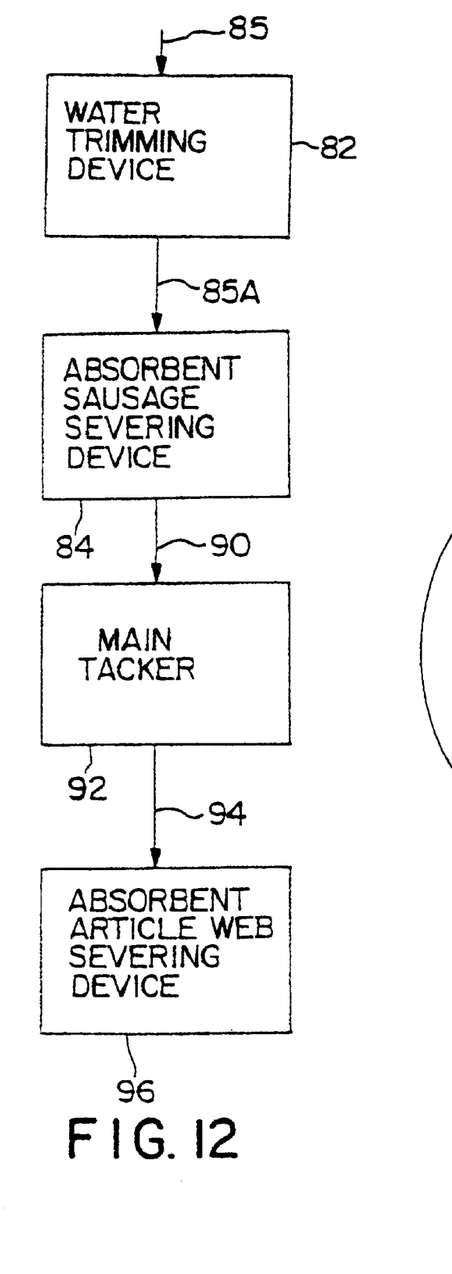
FIG. 12 shows a block diagram of further processing apparatus which act on the absorbent sausage of the invention to form an absorbent article.

Compressed gas supply 152 supplies compressed gas to gas heater 150. Gas heater 150 heats the compressed gas, such as air, to a desired gas temperature. Heated gas supply line 154 supplies the heated compressed gas to spray nozzle assembly 138. Spray nozzle assembly 138 deposits resin fiber 140 onto second surface 136 of absorbent sausage 120 to form a stabilization layer. Absorbent sausage 120 advances on transfer conveyor 157 to first and second nip rolls 158A, 158B comprising debulker 160. Debulker 160 varies the thickness of absorbent sausage 120 by controlling the compression force at the nip. From debulker 160, absorbent sausage 120 advances to transfer conveyor 162. Arrow 164 indicates a path leading absorbent sausage 120 to further processing stations. Exemplary such further processing stations are shown in FIG. 12 will be described in detail later.

Figure 8:
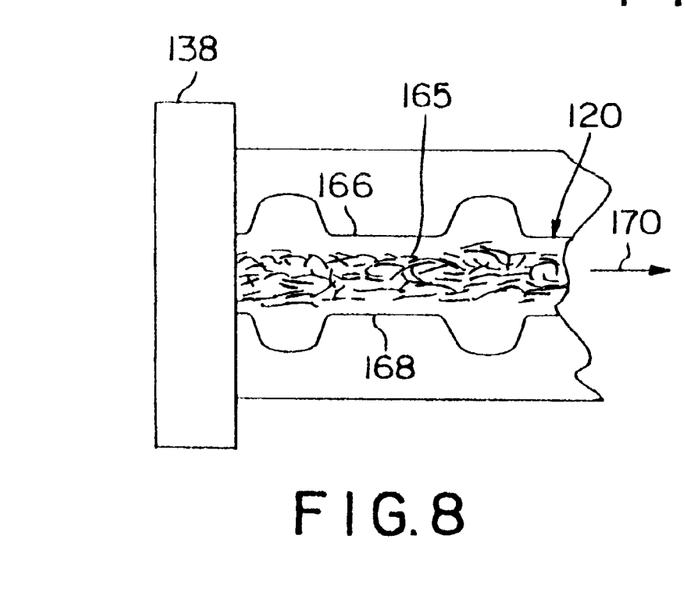
FIG. 8 shows a top view of a length of an absorbent sausage, taken at 8—8 of FIG. 7.
Figure 9:
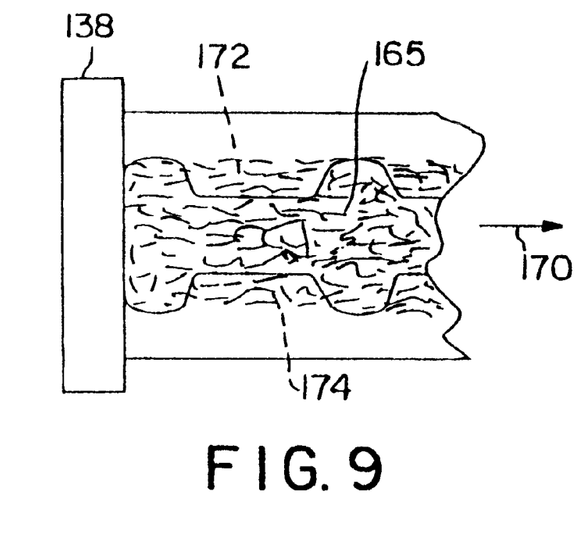
FIG. 9 shows a top view as in FIG. 8 wherein the resin has been applied over a greater width of the combination of the absorbent sausage and the containment layer.

FIG. 9 shows first and second opposing portions 172, 174 of containment layer 130 extend outwardly beyond respective edges 166, 168 of absorbent sausage 120. As shown in FIG. 8, for example, resin fiber 140 does not generally contact or reach containment layer 130.

In the embodiment of FIG. 9, spray nozzle assembly 138 sprays resin fiber 140 across substantially the entire width "W" of second surface 136 of absorbent sausage 120, optionally somewhat beyond the outer edges of the absorbent sausage, and onto at least part of first portion 172 and opposing second portion 174 of containment layer 130. As with the embodiment of FIG. 8, resin fiber 140 quickly cools and hardens, forming stabilization layer 165. Thus, containment layer 130 and stabilization layer 165 can, in combination, encompass absorbent sausage 120. Stabilization layer 165, of course, remains porous with respect to liquids.

Figure 10:
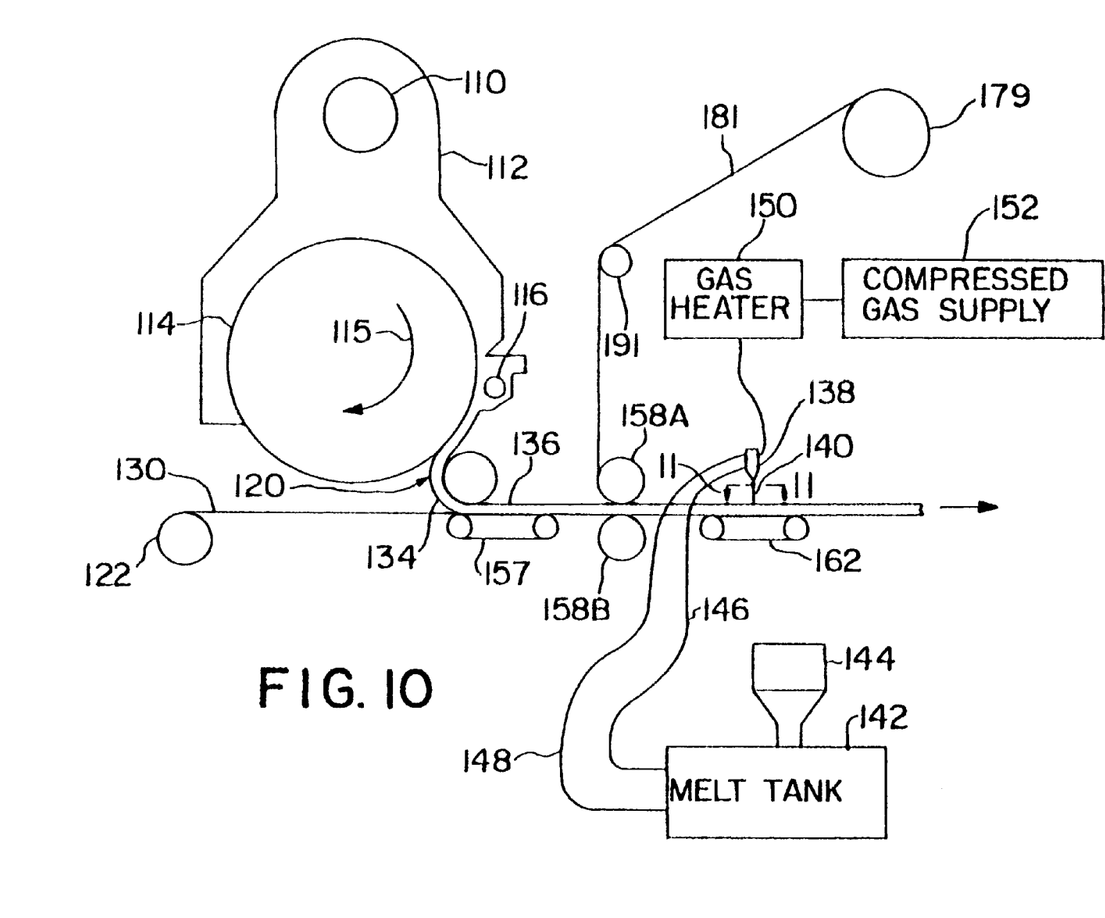
FIG. 10 shows another embodiment of the invention wherein a second containment layer is applied to the second surface of the absorbent sausage.

FIG. 10 discloses another embodiment of the invention. The embodiment of FIG. 10 is essentially the same as the embodiment in FIG. 7, except absorbent sausage 120 exits from the opposite side of forming drum 114 and more importantly, a supply roll 179 containing a second preformed containment layer 181 provides the second containment layer for the absorbent sausage. Further, the preferred arrangement of applying molten fibers 140 after debulker 160 is shown in FIG. 10. A first containment layer 130 is placed in surface-surface relationship with first surface 134 of absorbent sausage 120. Second containment layer 181 advances along a path and about turning roll 191 toward absorbent sausage 120. Second containment layer 181 is then applied in surface-to-surface relationship to second surface 136 of absorbent sausage 120 at nip rolls 158A, 158B.

Figure 11:
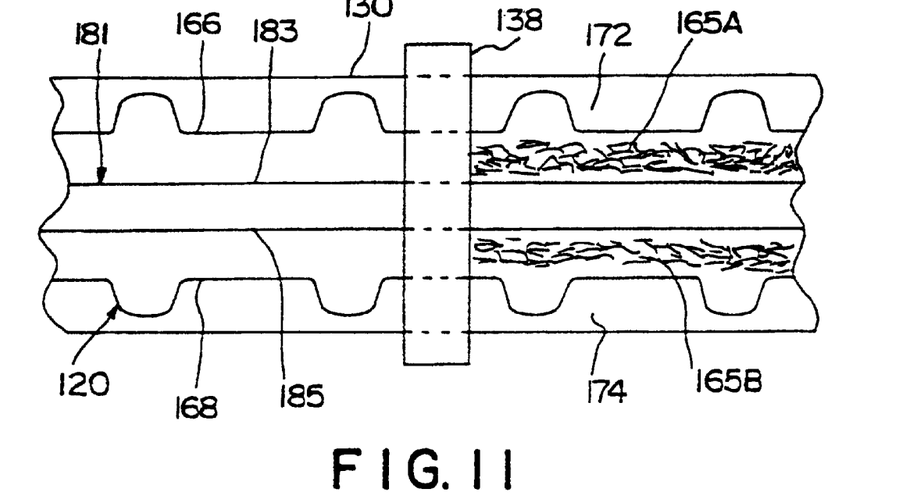
FIG. 11 shows a top view of a length of the absorbent sausage, and a spray nozzle assembly, taken at 11—11 of FIG. 10.

Second pre-formed containment layer 181 can comprise a narrow strip of forming tissue as shown in FIG. 11. Second preformed containment layer 181 can stabilize and support absorbent fluff of absorbent sausage 120. As shown in FIG. 11, second containment layer 181 comprises a narrow layer across a central portion of absorbent sausage 120. First and second edges 183, 185 of second containment layer 181 extend along the outside length thereof.

Second pre-formed containment layer 181 can have a width from about 2.5 inches to about 9 inches. An exemplary forming tissue has a porosity of approximately 400 cubic feet per minute per foot squared, and dry strength of about 730 grams.

Spray nozzle assembly 138 in FIG. 10 deposits resin fibers 140 onto absorbent sausage 120, second containment layer 181 and first and second portions 172, 174 of first containment layer 130. As shown in FIG. 11, nozzles in the middle and outer section of spray nozzle assembly 138 can be turned off, especially in a meltspray system, such that a first stabilization layer 165A of resin fibers 140 is applied to absorbent sausage 120 between outside edge 166 of absorbent sausage 120 and outside edge 183 of second pre-formed containment layer 181. Other nozzles of spray nozzle assembly 138 can simultaneous spray resin fiber 140 onto absorbent sausage 120 to form a second stabilization layer 165B between outside edge 168 of absorbent sausage 120 and outside edge 185 of second containment layer 181. In this manner, portions of absorbent sausage 120 not covered or supported by second pre-formed containment layer 181 can be stabilized. As shown in FIG. 11, the central region of absorbent sausage 120 in surface-to-surface relationship with second containment layer 181 need not have resin fibers 140 sprayed thereon. In some embodiments, adhesive can be applied to second containment layer 181 before placement onto absorbent sausage 120.

Figure 11A:
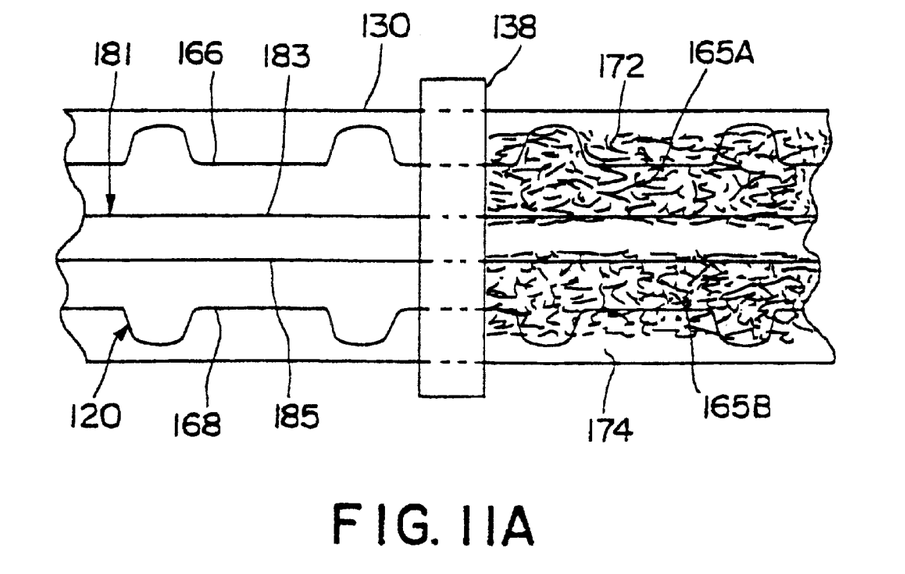
FIG. 11A shows a top view of a length of the absorbent sausage, and a spray nozzle assembly, taken at 11—11 of FIG. 10, the spray nozzle assembly spraying stabilization layers onto the first and second containment layers, and portions of the absorbent sausage.

In the embodiment of FIG. 11A, individual nozzles of spray nozzle assembly 138 can be controlled such that resin fibers are deposited onto first and second portions 172, 174 of first containment layer 130, as well as deposited on absorbent sausage 120. Further, individual nozzles can also be controlled such that resin fibers are deposited in contact with second containment layer 181 proximate outside edges 183, 185 thereof. Thus, the entire absorbent sausage 120 can be surrounded by containment layers 130, 181 and stabilization layers 165A, 165B of resin fiber material. Such an arrangement stabilizes the fluff material of absorbent sausage 120 and improves the integrity thereof. Surprisingly, the arrangement of FIGS. 10, 11 and 11A closely approximates the functional form of absorbent articles currently being manufactured, while significantly reducing cost of the absorbent articles by reducing the amount of containment layer material, such as forming tissue, needed to manufacture the absorbent article.

FIG. 12 shows exemplary further processing apparatus that forms absorbent articles which include absorbent sausage 20 as an element thereof. A combination of absorbent sausage 20, containment layer 30, and stabilization layer 65, is graphically represented by arrow 85 in FIG. 12.

Figure 13:
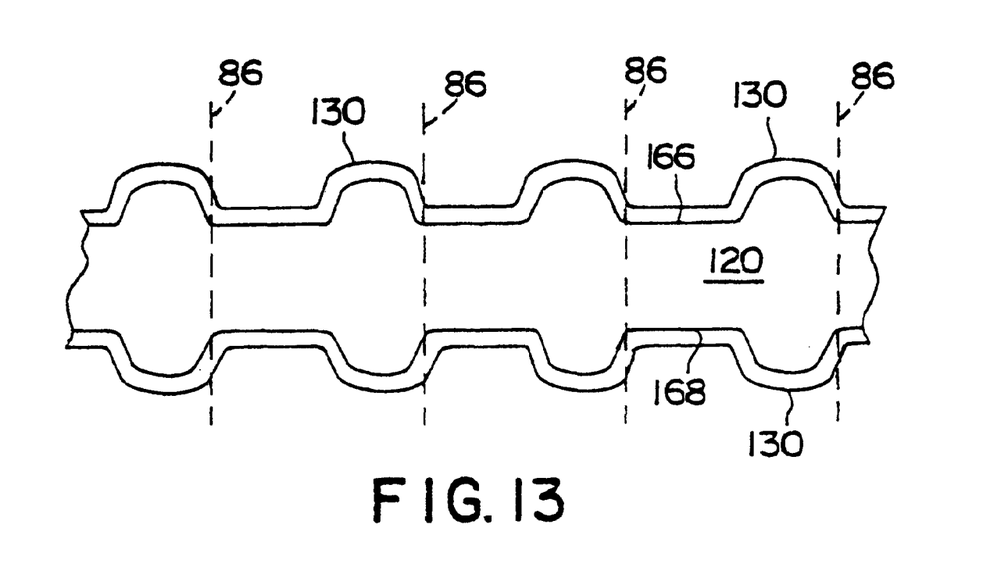
FIG. 13 shows a top view of a length of the absorbent sausage of the invention after portions of the containment layer have been trimmed away.

A water trimming device 82, or other conventional trimming device, trims excess material from first and second portions 172, 174 of containment layer 130 near outside edges 166, 168 of absorbent sausage 120 of FIG. 9. Water trimming device 82 follows the shape of absorbent sausage 120 corresponding to a "T". Preferably about a ½ inch width for each respective first and second portion 172, 174 of containment layer 130 is retained, extending outwardly from each respective outside edge 166, 168 of absorbent sausage 120. FIG. 13 shows absorbent sausage 120 after parts of first portion 172 and second portion 174 have been trimmed away. For purposes of illustration only, stabilization layer 165 is not shown in FIG. 13. In those embodiments where stabilization layer 165 is trimmed along with containment layer 130, a mechanical knife cutter preferably can be utilized, rather than water trimming device 182, in order to effectively cut resinous layer 165.

After trimming of containment layer 130, trimmed absorbent sausage 120 advances as graphically represented by arrow 85A in FIG. 12. Absorbent sausage severing device 84 then severs absorbent sausage 120, including layers 130 and 165, into individual absorbent pads. Dashed lines 86 in FIG. 13 show exemplary locations where absorbent sausage severing device 84 severs absorbent sausage 120 across its width to form individual absorbent pads 90. Absorbent pads 90 are graphically represented by arrow 90 in FIG. 14. Such absorbent sausage severing devices are well known in the art and include, for example, nip rolls having a cutting element mounted on one of the rolls thereon, and other conventional devices.

Figure 15:
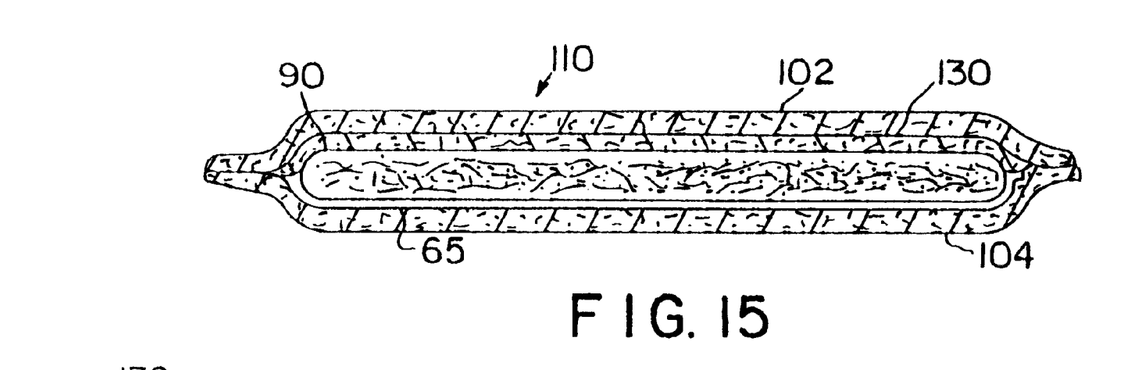
FIG. 15 shows a cross-sectional view of a completed absorbent article taken at 15—15 of FIG. 14.

Main tacker 92 mounts and secures discrete absorbent pads 90 between an outer cover and a bodyside liner to create an absorbent article sausage represented by arrow 94 in FIG. 12. Main tacker 92 is a conventional apparatus for forming absorbent articles on absorbent article sausage 94. Referring now to FIG. 14, preferably, hot melt adhesive is sprayed onto bodyside liner 102 and/or outer cover 104 (both shown in FIG. 15) to provide permanent securement of outer cover 104, bodyside liner 102, and absorbent pad 90, to each other at main tacker 92. Main tacker 92 includes a nip applying pressure to the several elements to ensure securement of the elements to each other. Absorbent pad 90, fed to main tacker 92, includes containment layer 130 and resinous stabilization layer 165 of fiber 140. While adhesive and pressure at the nip of main tacker 92 can secure the above elements, ultrasonic bonding and other methods of securement are contemplated as being acceptable.

Absorbent article web severing device 96 receives absorbent article sausage 94 as shown in FIG. 12, and severs the absorbent article web into individual absorbent articles 100.

FIG. 14 shows a complete absorbent article 100. Absorbent article 100 includes T-shaped absorbent pad 90 shown in dashed lines therein. Bodyside liner 102 comprises the surface of the absorbent article closest to the observer in the view of FIG. 14. A cross-sectional view of absorbent article 100, shown in FIG. 15, and taken across the width of the article of FIG. 14, shows the relationship between the various elements. A chassis formed by bodyside liner 102 and outer cover 104 encases, and thus encompasses, absorbent pad 90. Containment layer 130, comprising a barrier tissue, is located between bodyside liner 102 and absorbent pad 90. Containment layer 130 resists the return of liquid toward bodyside liner 102 after liquid passes therethrough into absorbent pad 90 and migration of superabsorbent material towards the user of the absorbent article. Stabilization layer 165 is located between absorbent pad 90 and outer cover 104 and is adjacent the outer cover. Stabilization layer 165 provides enhanced integrity to absorbent pad 90 and reduces the likelihood of exudates discoloring outer cover 104 of absorbent article 100. Stabilization layer 165 also assists in protecting outer cover 104 from being damaged or penetrated by material, especially particles of superabsorbent material migrating from absorbent pad 20C.

Other steps and apparatus for applying leg cuffs, waist bands, containment flaps, attachment ears, or the like are considered conventional and are within the scope of this disclosure. For example, a surge layer (not shown) can be located between bodyside liner 102 and containment layer 130. The surge layer allows exudates to spread over substantially the entire absorbent pad 90. Thus the surge layer assists absorbent pad 90 in absorbing a sudden large amount of urine.

Those skilled in the art will now see that certain modifications can be made to the invention herein disclosed with respect to the illustrated embodiments, without departing from the spirit of the instant invention. And while the invention has been described above with respect to the preferred embodiments, it will be understood that the invention is adapted to numerous rearrangements, modifications, and alterations, all such arrangements, modifications, and alterations are intended to be within the scope of the appended claims.

To the extent the following claims use means plus function language, it is not meant to include there, or in the instant specification, anything not structurally equivalent to what is shown in the embodiments disclosed in the specification.

Having thus described the invention, what is claimed is:

1. A system for fabricating an absorbent pad, said system comprising:
   (a) a forming device for forming material into an absorbent core having first and second opposing surfaces and first and second opposing edges;
   (b) a supply device for supplying a pre-formed containment layer against the first surface of the absorbent core; and
   (c) spray apparatus for spraying fibers of molten resin onto the second surface of the absorbent core, thereby depositing a permeable stabilization layer on the second surface such that the resin fibers interact with the absorbent core to increase the integrity of the absorbent core.

2. A system as in claim 1, said forming device having the capacity to form the absorbent core as a continuous absorbent sausage having a length, the absorbent sausage comprising a continuous air formed layer of fiber extending along the length thereof.

3. A system as in claim 1, said forming device including a fiberizer, a forming chamber and a rotatable forming drum for forming said absorbent core thereon.

4. A system as in claim 3, said forming device including a scarfing roll for shaving material from said absorbent core to reduce the thickness of said absorbent core.

5. A system as in claim 1, said spray apparatus comprising at least one nozzle having a resin aperture for exhausting resin therefrom, and multiple gas apertures for exhausting gas therefrom.

6. A system as in claim 5, said spray apparatus comprising a nozzle assembly having a plurality of said nozzles depositing molten resin onto the second surface of said absorbent core.

7. A system as in claim 6, said plurality of nozzles defining an array extending across the width of said formed absorbent core, and depositing the molten resin across a width of from about 2.5 inches to about 10 inches.

8. A system as in claim 1, aid spray apparatus comprising a meltspray assembly for directing the resin toward the second surface of the absorbent core as a spray of molten fibers.

9. A system as in claim 8, said meltspray assembly including a recirculation line for recirculating the resin from a melt tank such that the resin remains molten whether or not the spray apparatus is applying the resin as a spray of molten fibers.

10. A system as in claim 1, including a vacuum transfer device, said vacuum transfer device receiving the absorbent core from said forming device prior to application of the molten resin to the second surface.

11. A system as in claim 1, including a trimming device for trimming the containment layer from about the absorbent core.

12. A system as in claim 11, said forming device forming the absorbent core as a continuous length absorbent sausage, said system including a severing device for periodically severing said absorbent sausage into respective absorbent pads.

13. A system as in claim 12, including a main tacker for securing each respective absorbent pad between a respective bodyside liner and a respective outer cover, in forming an absorbent article, the stabilization layer being adjacent the outer cover.

14. A system as in claim 13, including a severing device for periodically severing the bodyside liner and the outer cover to form absorbent articles.

15. A system as in claim 1, first and second portions of the containment layer extending outwardly from the first and second opposing edges of the absorbent core, said spray apparatus depositing molten resin onto at least part of the first and second portions of the containment layer such that the molten resin cools and becomes hard, and interacts with the absorbent core at the second surface to increase the integrity of the absorbent core.

* * * * *